US00PP15281P2

(12) United States Plant Patent
Schlueter

(10) Patent No.: US PP15,281 P2
(45) Date of Patent: Oct. 26, 2004

(54) ***HIBISCUS ROSA-SINENSIS* PLANT NAMED 'NOVA'**

(50) Latin Name: *Hibiscus rosa-sinensis L.*
Varietal Denomination: Nova

(75) Inventor: Barry Schlueter, Houston, TX (US)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 10/764,188

(22) Filed: Jan. 23, 2004

(51) Int. Cl.[7] ..... A01H 5/00
(52) U.S. Cl. ..... Plt./257
(58) Field of Search ..... Plt./257

*Primary Examiner*—Kent Bell
(74) *Attorney, Agent, or Firm*—Christie, Parker & Hale LLP

(57) ABSTRACT

A new plant variety of *Hibiscus rosa-sinensis* named 'Nova', characterized by a heavy textured double flower with a bright yellow center, yellow veins, and shades of coral to orange throughout the body of the flower. It is a free-flowering plant with an upright, compact habit. The foliage is glossy and dark green.

3 Drawing Sheets

Botanical classification: *Hibiscus rosa-sinensis* L.
Varietal denomination: The new plant has the varietal denomination 'NOVA'.

BACKGROUND OF THE INVENTION

The present invention relates to a new and distinct variety of *Hibiscus rosa-sinensis* L., which was developed in a controlled breeding program in Webster, Tex.

The genus *Hibiscus* comprises about 250 species of herbs, shrubs and trees in warm temperate and tropical regions; with leaves usually simple, mostly palmately veined, lobed or parted; flowers mostly solitary in the leaf axils but sometimes in racemes, corymbs or panicles. *Hibiscus* is included in the family Malvaceae, which comprises about 95 genera of herbs, shrubs and trees originating in tropical and temperate regions. *Hibiscus rosa-sinensis* is a glabrate shrub, seldom over 8 feet tall in cultivation, but treelike to 15 feet or more in tropical regions. Leaves to 6-inches long, ovate, usually serrate, mostly glossy green. Flowers solitary in upper leaf axils.

The new *Hibiscus* is a product of a planned breeding program conducted by the inventor in Webster, Tex. The objective of the program was to create new *Hibiscus* selections with improved bloom quality, color and floriferousness, plants that can be commercially produced on their own root systems, and improved plant habit with regard to vigor and postproduction longevity.

The new *Hibiscus* originated from a cross-pollination made by the Inventor using 'Green Hornet' (not patented) as the female parent and 'Red Snapper' (not patented) as the male parent. The new *Hibiscus* was discovered and selected by the Inventor as a plant within the progeny of the stated cross-pollination in a controlled breeding program in Webster, Tex.

SUMMARY OF THE INVENTION

The new variety was discovered in a controlled breeding program of *Hibiscus rosa-sinensis* and differs from its parents and other known cultivars of *Hibiscus rosa-sinensis* by the following characteristics in combination:

1. Upright, compact symmetrical plant habit that is suitable for container production;
2. Healthy green foliage;
3. Vigorous growth habit;
4. A heavy textured double flower with a bright yellow center, yellow veins and shades of coral to orange throughout the body of the flower;
5. Free-flowering.

Asexual reproduction of the new variety by stem cuttings, performed in Webster, Tex. and Fulshear, Tex. have confirmed that the distinctive characteristics of the new variety are stable and transmitted to succeeding generations, and the new variety reproduces true to type.

COMPARISON WITH PARENTS AND OTHER CULTIVARS

'Nova' is distinguished from its female parent 'Green Hornet' (not patented) by having a different flower form and color; 'Green Hornet' has a single and greenish yellow bloom. 'Nova' is distinguished from its male parent 'Red Snapper' (not patented) by a dissimilarity of flower color, flowers of 'Red Snapper' are red and white. Also, the flower petals of 'Red Snapper' do not overlap as nicely as the petals of 'Nova'; consequently, flowers of 'Nova' have a much fuller appearance.

Plants of 'Nova' can be compared to plants of the cultivar 'Jimmy John' (not patented). However, in side-by-side comparisons conducted in Webster, Tex., plants of 'Nova' differ from plants of the cultivar 'Jimmy John' in the following characteristics:

1. Flowers of 'Nova' are brighter in color than flowers of 'Jimmy John';
2. Plants of 'Nova' are easier to propagate via vegetative cuttings than plants of the cultivar 'Jimmy John'.

BRIEF DESCRIPTION OF ILLUSTRATIONS

The accompanying illustrations show a specimen of the new cultivar in a photographic illustration as true to color as is reasonably possible to make in an illustration of this character.

DETAILED DESCRIPTION OF THE NEW VARIETY

Figure 1:
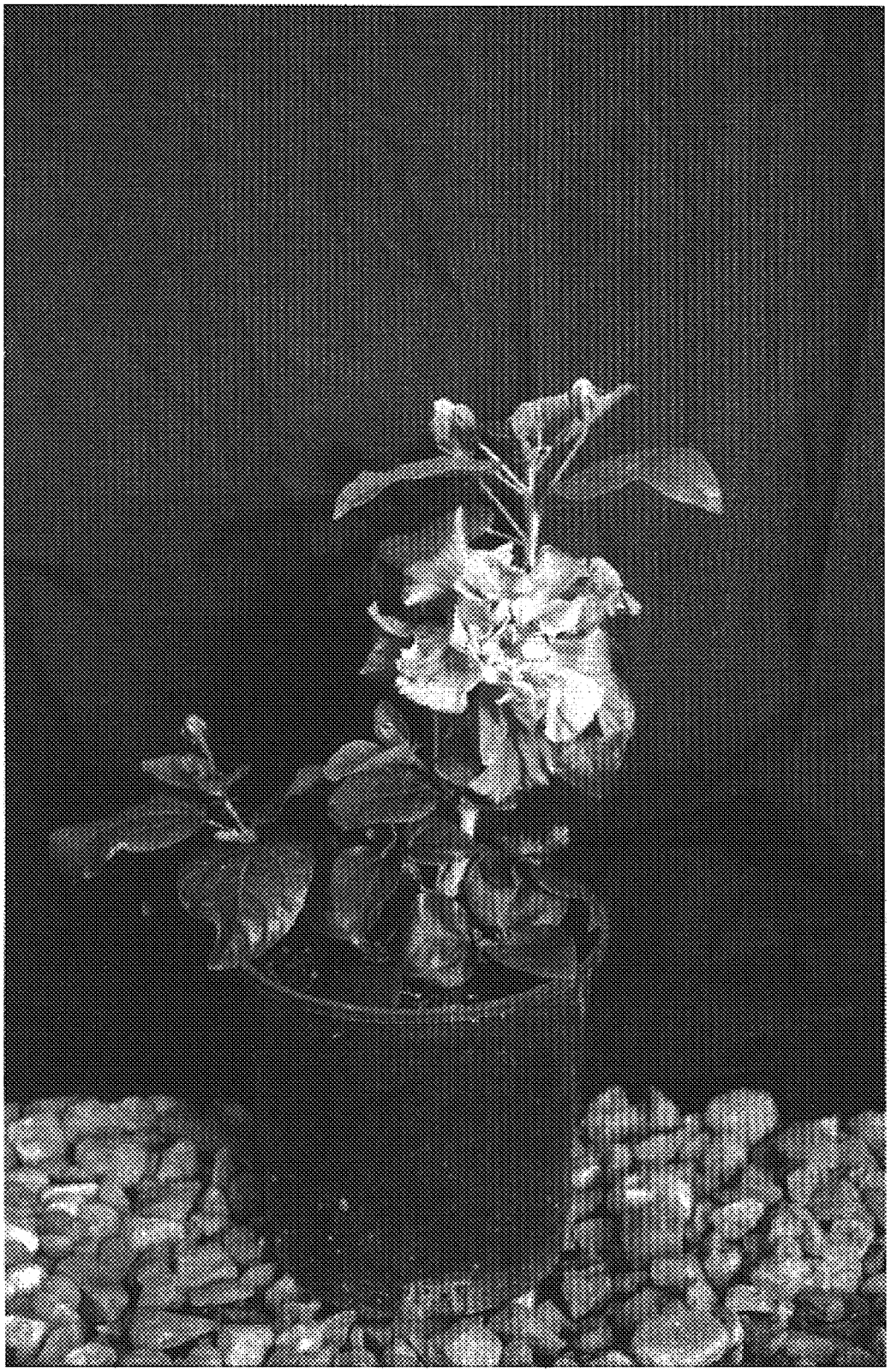
FIG. 1 illustrates a side perspective view of a typical plant of 'Nova'.
Figure 2:
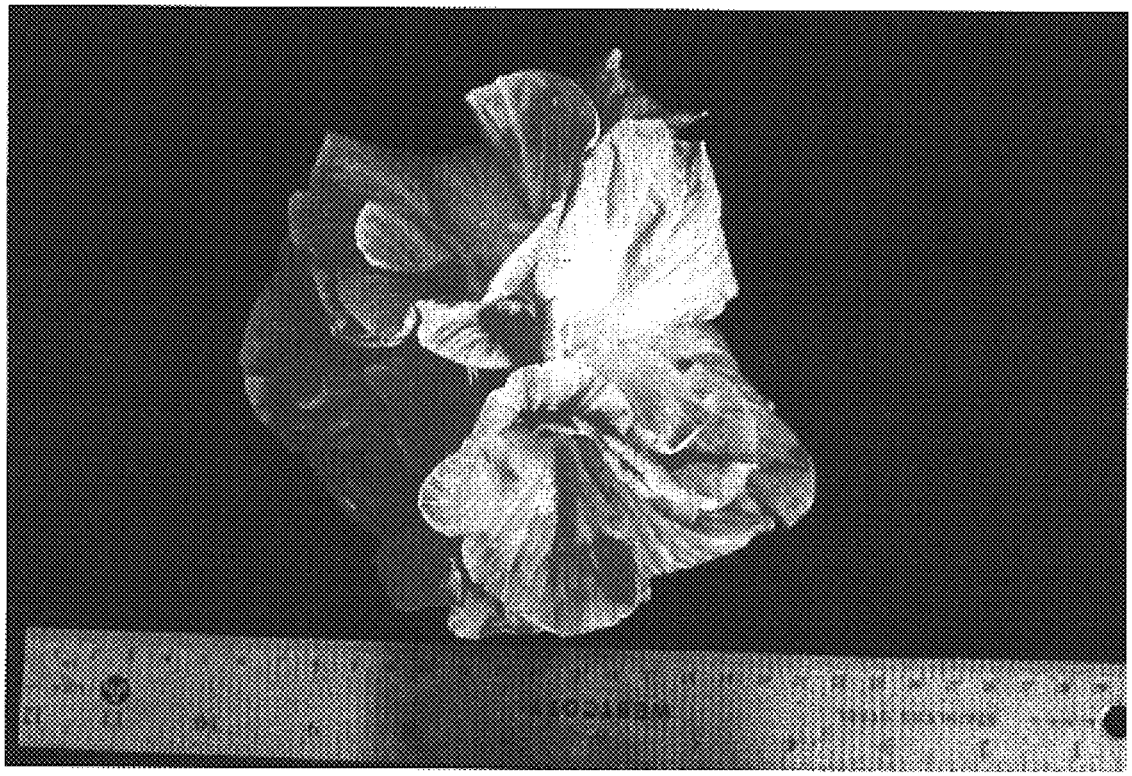
FIG. 2 illustrates the scale of a typical flower of 'Nova'.
Figure 3:
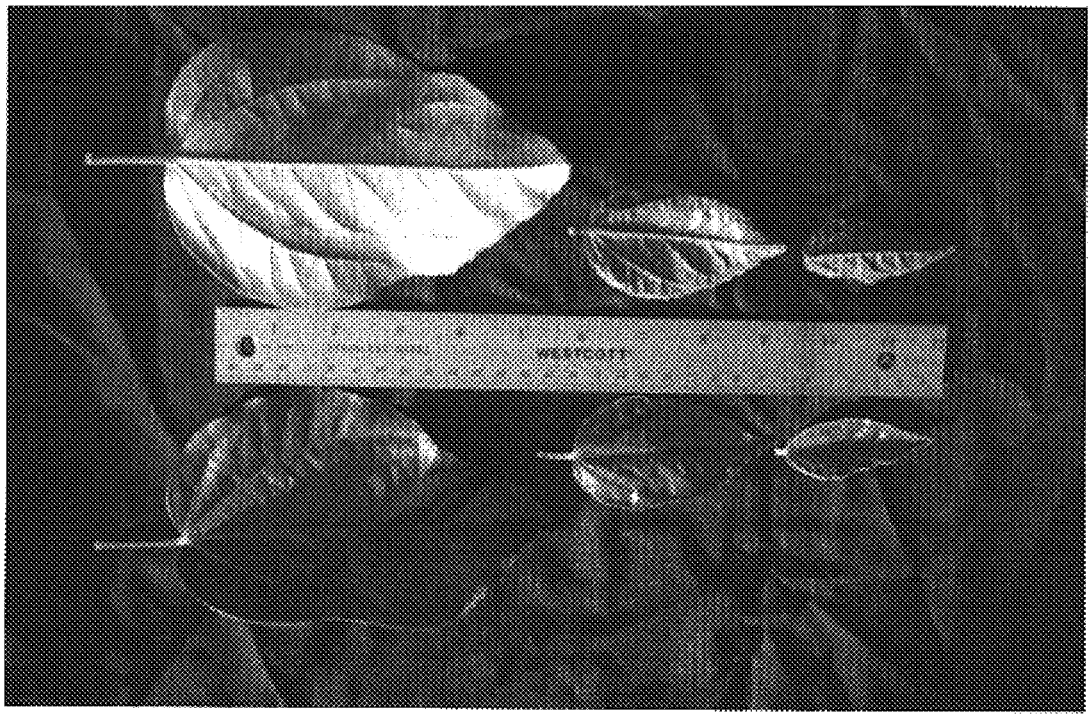
FIG. 3 illustrates the typical young to mature foliage of 'Nova'; the abaxial and adaxial surfaces are shown at each stage.

'Nova' has not been observed under all possible environmental, cultural and light conditions. The following observations and descriptions are of plants grown in Fulshear, Tex., in November 2003, under polypropylene shadecloth providing a 30 percent light reduction, and under conditions which closely approximate commercial production. Plants described were approximately one year old and in a #3 nursery container. In this description, color references are to The Royal Horticultural Society Colour Chart (2000) and terminology used in the color descriptions herein refers to plate numbers in this color chart. Phenotypic expression may vary with light intensity, cultural and environmental conditions.

CLASSIFICATION

Botanical: *Hibiscus rosa-sinensis* L. 'Nova'.

Parentage:

*Female or seed parent.*—*Hibiscus rosa-sinensis* 'Green Hornet' (not patented).

*Male or pollen parent.*—*Hibiscus rosa-sinensis* 'Red Snapper' (not patented).

Propagation: By stem cuttings.

Time to initiate rooting: Approximately 14 to 21 days at 21–24 C.

Time to develop roots: Approximately 42 to 56 days at 21–24 C.

Root description: Fine to medium; fibrous; freely branching.

PLANT

Size:

*Height.*—Approximately 51 cm from soil level to top of flowers.

*Diameter/spread.*—Approximately 60 cm.

Form and growth habit: Perennial, evergreen shrub; mostly upright and somewhat spreading.

Branching: Freely branching; approximately 4 to 8 lateral branches develop after pinching.

*Lateral branches.*—Approximately 20 cm long and 5 mm in diameter.

*Internode length.*—Approximately 4 cm.

LEAF

Shape: Ovate.

*Apex.*—Obtuse.

*Base.*—Cordate.

Leaf size: Approximately 8.5 cm long and 10.5 cm wide.

Arrangement: Alternate, single; symmetrical.

Margin: Entire.

Aspect: Undulate.

Texture/substance: Glabrous, shiny.

Coloration:

*Young foliage.*—Upper side: Near Yellow-Green Group 146A. Under side: Near Yellow-Green Group 146B.

*Mature foliage.*—Upper side: Near Yellow-Green Group 147A. Under side: Near Yellow-Green Group 147B.

Petioles:

*Size.*—Approximately 3.5 cm long, 3 mm across.

*Coloration.*—Near Yellow-Green Group 147B.

*Texture.*—Smooth.

Hardiness: USDA Zone 10 (30° F. to 40° F.).

Pests/diseases: Resistance to known *Hibiscus* diseases had not been observed on plants grown under conditions approximating commercial practices.

INFLORESENCE

Bloom period: Typically year-round under subtropical and tropical conditions.

Flower arrangement: Arranged singly at terminal leaf axils; free-flowering with 3 to 4 flower buds and/or open flowers per terminal apex; flowers face upright and slightly outward.

Flower appearance: A heavy textured double flower with bright yellow centers, yellow veins and shades of coral to orange throughout the body of the flower; flowers are open for about two days before closing; flowers persistent.

Flower diameter: Approximately 17 cm.

Buds (just prior to showing color):

*Rate of opening.*—Approximately 1 or 2 days, depending on temperature.

*Shape.*—Elliptic.

*Length.*—Approximately 3.5 cm.

*Diameter.*—Approximately 2.5 cm.

*Color.*—Near Yellow-Green Group 144C.

Fragrance: None noted.

Petals:

*Number/arrangement.*—Corolla consists of approximately 30 to 35 petals.

*Shape.*—Spatulate with rounded apex.

*Length.*—Range from approximately 7 to 9 cm.

*Width.*—Range from approximately 3 to 6.5 cm.

*Margin.*—Entire, but ruffled.

*Texture.*—Smooth. Color: Upper Surface: The centers range from near Yellow Group 13B to 13C. The coral to orange portion of the petals range from near Orange-Red Group 34A through 35A; venation on the petals is near Yellow-Orange Group 18A. Lower Surface: The majority ranges from near Orange-Red Group N34B to 35C, eventually fading to either Yellow-Orange Group 20A or Yellow Group 10C at the base of the petal.

*Sepals.*—Number/Arrangement: 5 sepals fused into a star-shaped calyx. Shape: Linear with acuminate apices. Margin: Entire. Color: Near Yellow-Green Group 144A.

*Peduncles.*—Length: Approximately 4 cm. Diameter: Approximately 2 mm. Angle: Approximately 90 degrees. Strength: Strong, flexible. Color: Near Yellow-Green Group 144B.

REPRODUCTIVE ORGANS

Androecium:

*Stamens.*—Numerous; approximately 50. Stamen Length: Approximately 5 mm. Filament Color: Near Yellow Group 4C.

*Anther length.*—Approximately 1 mm.

*Pollen amount.*—Abundant.

*Pollen color.*—Yellow Group 13B.

Gynoecium:

*Pistil number.*—1.

*Pistil length.*—Approximately 6 cm.

*Stigma appearance.*—5, rounded.

*Stigma diameter.*—Approximately 2 mm.

*Stigma color.*—Near Orange Group N25A.

*Style color.*—Near Yellow-Orange Group 18A.

*Seed production.*—Seed production has not been observed.

I claim:

1. A new variety of *Hibiscus rosa-sinensis* plant as shown and described.

* * * * *